(12) United States Patent
Dragan et al.

(10) Patent No.: US 6,869,419 B2
(45) Date of Patent: Mar. 22, 2005

(54) UNIT DOSE LOW VISCOSITY MATERIAL DISPENSING SYSTEM INCLUDING SYRINGE WITH BREACH

(75) Inventors: William B. Dragan, Easton, CT (US); Gordon Rowe, Wallingford, CT (US)

(73) Assignee: Centrix, Inc., Shelton, CT (US)

( * ) Notice: Subject to any disclaimer, the term of this patent is extended or adjusted under 35 U.S.C. 154(b) by 235 days.

(21) Appl. No.: 09/969,340

(22) Filed: Oct. 1, 2001

(65) Prior Publication Data

US 2002/0010430 A1 Jan. 24, 2002

Related U.S. Application Data

(62) Division of application No. 09/399,891, filed on Sep. 21, 1999, now Pat. No. 6,328,715.

(51) Int. Cl.[7] .................. A61M 5/178; A61M 5/315; A61M 5/00
(52) U.S. Cl. .................. 604/217; 604/218; 604/232
(58) Field of Search .................. 604/232, 212, 604/214–217, 218–222, 234, 235; 433/89, 90, 87, 80; 222/92, 95, 100, 105, 165

(56) References Cited

U.S. PATENT DOCUMENTS

| | | | | |
|---|---|---|---|---|
| 937,029 A | * | 10/1909 | Strong | 604/204 |
| 2,514,575 A | * | 7/1950 | Hein | 604/202 |
| 2,805,662 A | * | 9/1957 | Lawshe et al. | 604/204 |
| 2,890,698 A | * | 6/1959 | Sloane | 604/204 |
| 2,994,323 A | | 8/1961 | Dann et al. | |
| 3,884,231 A | | 5/1975 | Peters | |
| 3,900,954 A | * | 8/1975 | Dragan | 433/90 |
| 3,955,719 A | | 5/1976 | Pheuipin | |
| 4,392,491 A | | 7/1983 | Takasugi et al. | |
| 4,472,141 A | * | 9/1984 | Dragan | 433/90 |
| 4,738,379 A | * | 4/1988 | Takasugi | 222/95 |
| 4,795,444 A | | 1/1989 | Hasegawa et al. | |
| 4,972,969 A | | 11/1990 | Randklev | |
| 5,129,825 A | | 7/1992 | Discko, Jr. | |
| 5,320,257 A | | 6/1994 | Snedden | |
| 5,346,481 A | | 9/1994 | Bunin | |
| 5,489,207 A | | 2/1996 | Dragan et al. | |
| 5,609,580 A | * | 3/1997 | Kwiatkowski et al. | 604/212 |
| 5,827,233 A | | 10/1998 | Futagawa et al. | |
| 6,248,094 B1 | * | 6/2001 | Epperson | 604/195 |
| 6,435,373 B1 | * | 8/2002 | Mizrahi | 222/105 |
| 6,485,459 B1 | * | 11/2002 | Surowitz | 604/110 |

FOREIGN PATENT DOCUMENTS

| | | |
|---|---|---|
| DE | 217162 | 4/1908 |
| DE | 7837177 | 3/1979 |
| DE | 33 44 345 A1 | 6/1985 |
| DE | 44 19 235 A1 | 12/1995 |
| DK | 32825 | 1/1924 |
| EP | 0 919 206 A2 | 6/1999 |
| GB | 787090 | 12/1957 |

* cited by examiner

*Primary Examiner*—Nicholas D. Lucchesi
*Assistant Examiner*—Catherine S. Williams
(74) *Attorney, Agent, or Firm*—Fattibene Fattibene; Paul A. Fattibene; Arthur T. Fattibene

(57) ABSTRACT

An ampule having a body portion and a sealed end portion and a sealed delivery portion adapted for use in a delivery syringe system for controllably dispensing a low viscosity material, such as a liquid, gel, or paste. An ampule having sealed rear portions adapted to mate with a plunger of a syringe so as to facilitate controlled dispensing of a low viscosity material. The syringe has a breach positioned to provide controlled flow of the dispensed low viscosity material and facility easy removal from the syringe. Low viscosity materials, such as liquids and gels, are controllably dispensed in a measured unit dose quantity. The present invention has many applications, but is particularly applicable to dispensing low viscosity materials such as used in coatings and not injected parenterally, and is particularly applicable to dental applications.

11 Claims, 6 Drawing Sheets

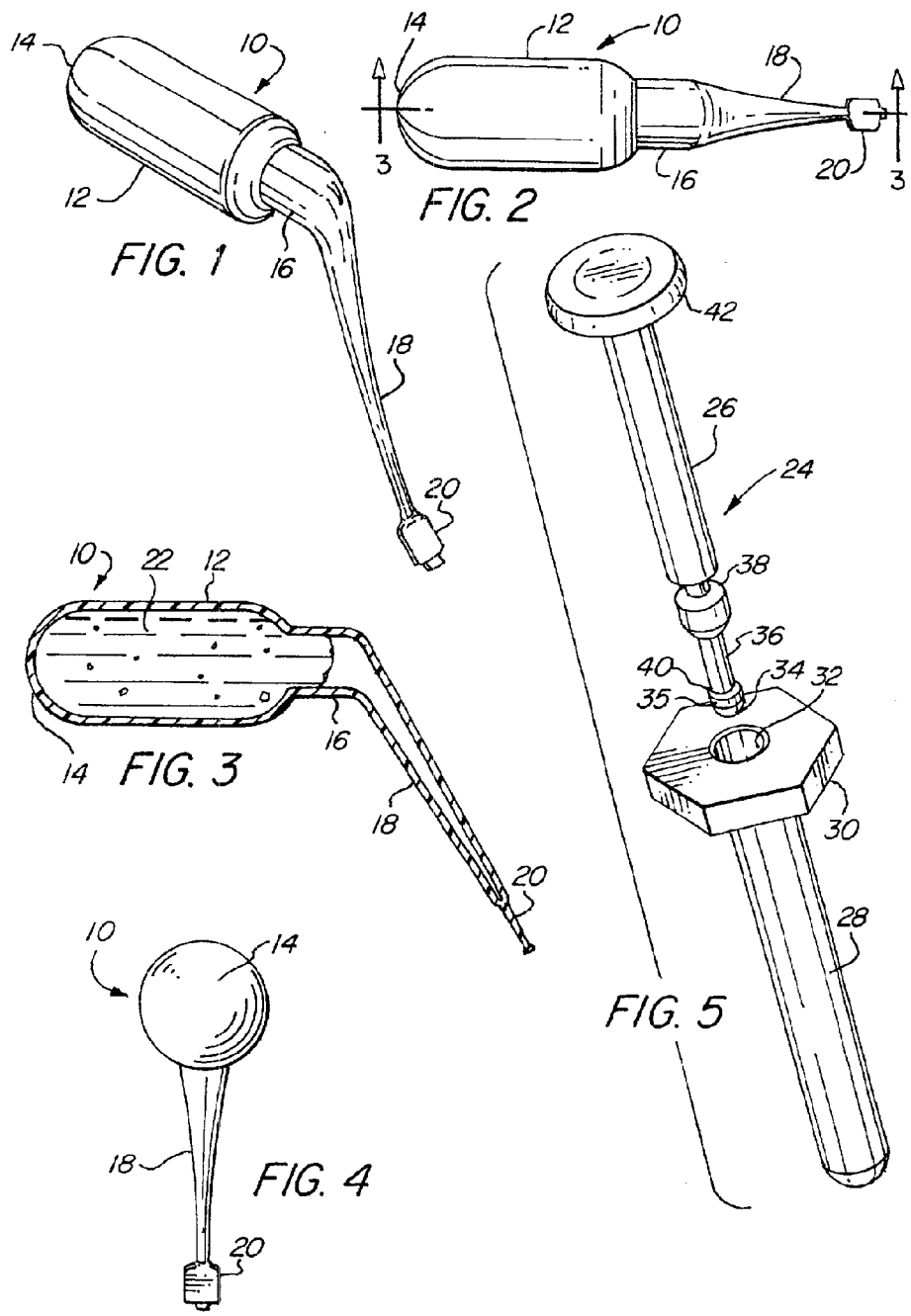

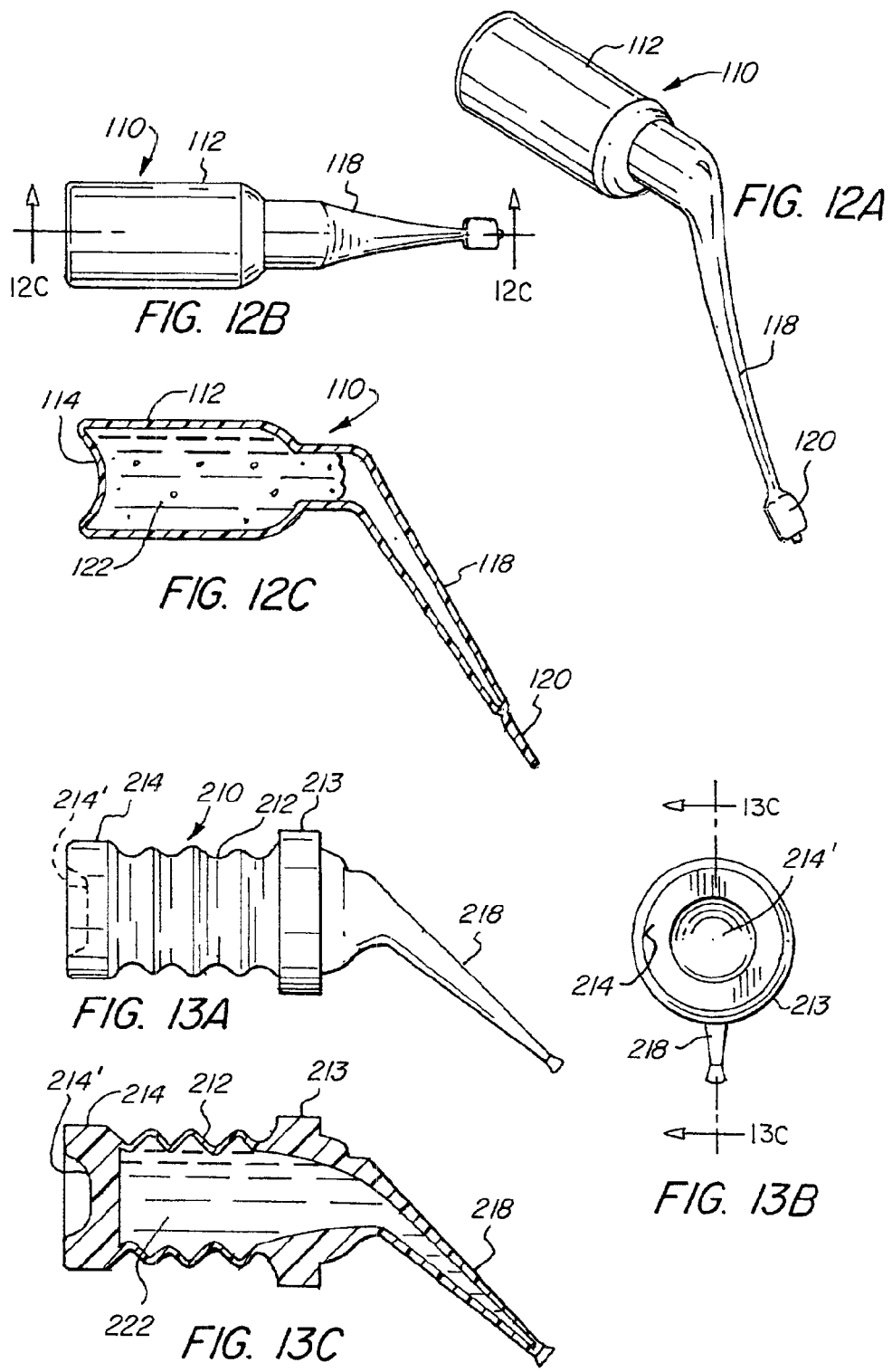

UNIT DOSE LOW VISCOSITY MATERIAL DISPENSING SYSTEM INCLUDING SYRINGE WITH BREACH

RELATED APPLICATION

This application is a divisional of U.S. patent application Ser. No. 09/399,891 filed Sep. 21, 1999, now U.S. Pat. No. 6,328,715, which is herein incorporated by reference.

FIELD OF THE INVENTION

The present invention relates in general to the placement of low viscosity material, and particularly to a collapsible cartridge or ampule and syringe for dispensing low viscosity material.

BACKGROUND OF THE INVENTION

In many applications, such as medical or industrial applications, and in particular dentistry, it is desirable to place accurately a low viscosity material. In dentistry in particular, there are many devices to apply a high viscosity material such as various cartridges and syringes. For example, a cartridge for dispensing a high viscosity material is disclosed in U.S. Pat. No. 4,963,093 entitled "Dental Syringe Tip And Syringe Holder Therefor" issuing to Dragan on Oct. 16, 1990. Therein disclosed is a syringe tip constructed to minimize the entrapment of air by the material being extruded. The cartridges generally contain relatively viscous material requiring a syringe having a mechanical advantage for dispensing the material. Such a syringe is disclosed in U.S. Pat. No. 5,125,836 entitled "Easy Loading Manual Extruder For Viscous Material" issuing to Dragan et al on Jun. 30, 1992. Therein disclosed is a syringe having a mechanical advantage used in dispensing material from a cartridge. While the devices disclosed in these patents provide easy dispensing of relatively high viscosity materials which are difficult to extrude, there is often a need to dispense low viscosity materials, such as fluids and gels, in a controlled manner. Generally, low viscosity materials are applied on a surface or large cavity, that is not parenterally. Often, dispensing of these relatively low viscosity materials, including fluids and gels, is done by brushing or dabbing with a hand held applicator. One such applicator system is disclosed in U.S. Pat. No. 5,660,273 entitled "Single Patient Dose Medicament Dispenser With Applicator" issuing to Discko, Jr. on Aug. 26, 1997. Therein disclosed is a tray having wells or depressions therein for holding a medicament or material and an applicator, such as a brush, for dispensing the medicament or material. Another technique for dispensing relatively small volumes of low viscosity material is by placing a quantity of the low viscosity material into a dropper type device which may be sealed, such as an ampule. One such device is disclosed in U.S. Pat. No. 5,320,257 entitled "Resilient Ampule With Articulating Linkage And Elongated Spout" issuing to Snedden on Jun. 14, 1994. Therein disclosed is an elongated ampule having a reservoir bulb on one end and an elongated spout on the other end with an articulating linkage or bellows therebetween.

While many of these prior devices have adequately dispensed material, there is a need for an improved and more convenient apparatus and method for dispensing low viscosity materials economically and in a controlled manner with a single dose system.

SUMMARY OF THE INVENTION

The present invention is a delivery system for controllably dispensing a low viscosity material, such as a liquid or a gel, in a single or unit dose. The ampule having a body with a sealed end and a dispensing end having a nozzle which has a removable seal. The ampule is made of a flexible collapsible material such as a pliable plastic. The material contained within the ampule is sealed and is of sufficient quantity for a single dose. A syringe has a structure to facilitate removal of the expended collapsed ampule. One embodiment of the invention has a syringe having a plunger adapted to controllably dispense the liquid or gel material contained within the ampule and is shaped or dimensioned to facilitating easy removal of the expended collapsed ampule. In another embodiment the syringe has a breach positioned to facilitate easy insertion and removal of the ampule. In another embodiment the syringe has multiple internal diameters to facilitate removal of the expended ampule. The ampule and syringe combination provides economical and controlled dispensing of a low viscosity liquid or gel in a unit dose. Any low viscosity material may be dispensed, but the present invention is particularly applicable to dispensing medical materials, including dental materials, such as adhesives, sealants, etches, or other material to be applied non parentally.

Accordingly, it is an object of the present invention to provide a unit dose dispensing system for low viscosity materials, such as liquids and gels, for both medical and industrial use.

It is another object of the present invention to provide controlled dispensing of relatively small volumes of low viscosity materials.

It is an advantage of the present invention that a unit measured dose of low viscosity material can be dispensed economically.

It is another advantage of the present invention that the collapsed expended ampule is easily removed from the barrel of a syringe.

It is yet another advantage of the present invention allows for controlled flow and placement of material without spurting and also improves visibility during dispensing.

It is a feature of one embodiment of the present invention that the end of a plunger is shaped so as to grasp the collapsed expended ampule, facilitating easy removal.

It is another feature of one embodiment of the present invention that a breach is positioned relative to the ampule, facilitating extrusion or dispensing of the low viscosity material.

It is yet another feature of one embodiment of the present invention that the internal diameters of the barrel facilitates dispensing of the material contained within the ampule and removal of a collapsed expended ampule.

These and other objects, advantages and features will become readily apparent in view of the following more detailed description.

BRIEF DESCRIPTION OF THE DRAWINGS

FIG. 1 is a perspective view of an ampule.

FIG. 2 is a plan view of the ampule illustrated in FIG. 1.

FIG. 3 is a cross sectional view taken along line 3—3 in FIG. 2.

FIG. 4 is a rear elevational view of the ampule illustrated in FIG. 1.

FIG. 5 is a perspective view of a dispensing syringe.

FIG. 12A is a perspective view of another embodiment of an ampule of the present invention.

FIG. 12B is a plan view of the ampule illustrated in FIG. 12A.

FIG. 12C is a cross section taken along lines 12C—12C in FIG. 12B.

FIG. 13A is a side elevational view of another embodiment of an ampule of the present invention.

FIG. 13B is a rear elevational view of the ampule illustrated in FIG. 13A.

FIG. 13C is a cross section taken along line 13C—13C in FIG. 13B.

DETAILED DESCRIPTION OF THE PREFERRED EMBODIMENTS

Figure 6A:
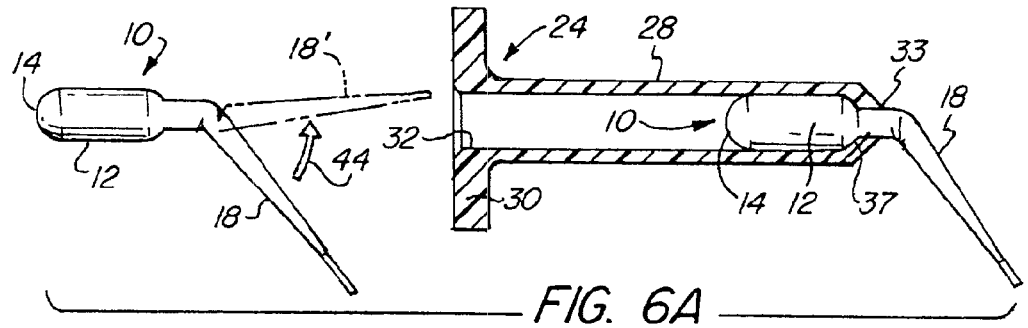
FIGS. 6A–C are partial cross sectional views illustrating operation of the present invention.

FIG. 1 is a perspective view illustrating an ampule 10. The ampule 10 may be made of any suitable collapsible or flexible material such as a plastic, including polypropylene, polyethylene, and other moldable plastics. The plastic may be selected from any type of material with suitable properties such that it does not react with the material contained therein or it does not change the properties of the material due to absorption of any component of the material. The ampule 10 has a body 12 with a hemispherical sealed end 14 and a dispensing end 16. The dispensing end 16 has a nozzle or spout 18. One end of the nozzle 18 is sealed with a seal 20 which may is removable, either by cutting off, breaking off, snapping off, or twisting off the seal 20. Additionally, the nozzle 18 may be sealed with a plug or other equivalent seal. A low viscosity material such as a liquid, gel or paste is sealed within the ampule 10. By low viscosity it is meant any material having a viscosity such that when expressed, extruded or forced from the ampule 10, the flexible or pliable material of the ampule 10 will not unintentionally rupture. The viscosity of liquids, gels, or pastes may be such as to be able to be used in the capsule or ampule 10. This would be dependent on the type of plastic and the mechanical advantage, if any, needed to express the material.

FIG. 2 is a plan view more clearly illustrating the ampule 10. FIG. 3 is a cross sectional view taken along lines 3—3 in FIG. 3 illustrating material placed within the ampule 10. FIG. 4 is a rear elevational view more clearly illustrating the ampule 10.

Referring to FIGS. 2–4, the body 12 of the ampule 10 is readily collapsible such that the low viscosity material 22 can be dispensed through nozzle 18 when seal 20 is removed. The seal 20 may be any convenient seal for sealing the end of the nozzle 18. The nozzle 18 preferably is elongated and at an angle such that placement of the material 22 is facilitated. The nozzle 18 is sufficiently flexible such that it could be moved into an axial position relative to the body portion 12.

FIG. 5 is a perspective view illustrating a syringe used to dispense the material in the ampule 10 illustrated in FIGS. 1–4. The use of a dispenser syringe 24 greatly facilitates the ease and control within which the material within an ampule may be dispensed. The dispenser syringe 24 comprises a plunger 26 adapted to be received by a barrel 28 through opening 32. Adjacent opening 32 is a flange 30. The plunger 26 has a plunger tip 34 and a reduced diameter portion 36. A shoulder 40 is formed between the reduced diameter portion 36 and the plunger tip 34. The plunger tip 34 may be hemispherical. A land 35 may be positioned between the shoulder 40 and the hemispherical plunger tip 34. Additionally, on the plunger 26 is a groove 38. The groove 38 may be used to hold an O-ring to provide a seal or friction between the inner diameter of the barrel 28 and the plunger 26. An O-ring type seal may also be molded into or formed integrally from the material of the plunger 26. A pad 42 is placed on one end of the plunger 26 to facilitate dispensing.

Figure 6B:
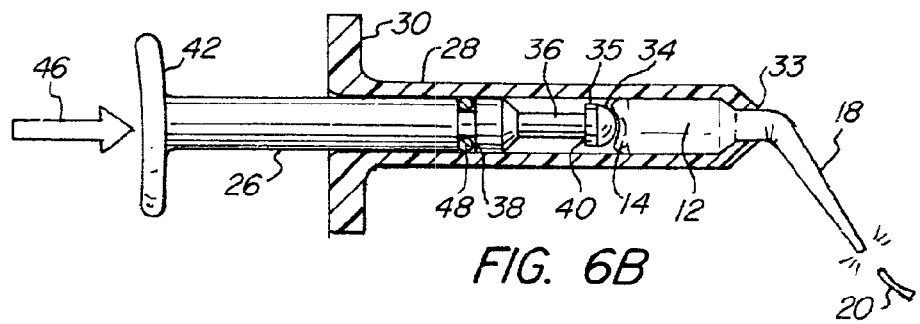
Figure 6C:
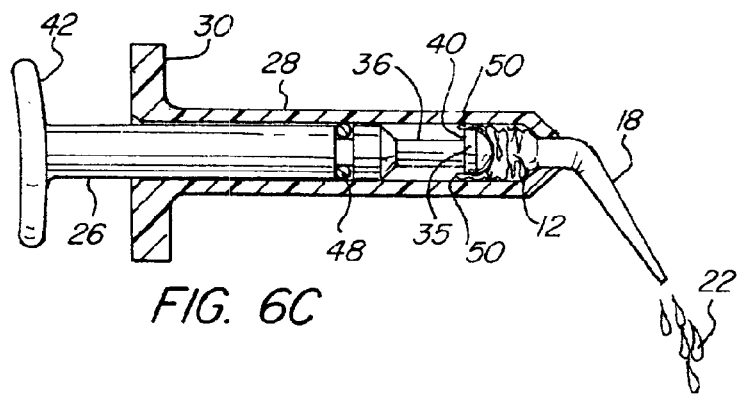

FIGS. 6A–C illustrate the operation of the present invention and ease in which a material can be dispensed. FIG. 6A illustrates an ampule being loaded into the opening 32 in the rear end of the barrel 28. Nozzle 18 is flexible and easily moved into an axial position in a direction of arrow 44 illustrated in phantom at 18'. The body portion 12 should have a diameter nearly equal to or slightly less than the internal diameter of the barrel 28. The nozzle 18 is directed by inclined surface 37 through an opening 33.

FIG. 6B illustrates the insertion of the plunger 26 into the barrel 28 and advancing the plunger in the direction of arrow 46. An O-ring 48 may be placed in the groove 38 within the plunger 26 so as to provide a friction resistance or a seal. Upon removal of the seal 20 on the end of the nozzle 18, and the advancing of the plunger 26, the plunger tip 34, being hemispherical, collapses the hemispherical end 14 of the ampule causing the body portion 12 to collapse and roll over the plunger end 34 and the land 35. The relatively low viscosity material is thereby dispensed from the body 12 of the ampule. The dispensing of the material is precisely controlled. Additionally, the syringe dispenser 24 helps to extend the reach and placement of material, especially within difficult to reach areas, such as the mouth in dental applications. The syringe dispenser 24 also greatly improves visibility within small openings, such as the mouth.

FIG. 6C illustrates the dispensing of a material 22 from the nozzle 18 and the collapse of the body portion 12. The diameter of the land 35 on the plunger end is such that there is a gap between the internal diameter of the barrel 28 permitting a portion 50 of the collapsed body portion 12 of the ampule to fit between the internal diameter of the barrel 28 and the land portion 35 of the plunger end. This gap should be between one and two times the wall thickness of the ampule 10. The material of the collapsed ampule 50 is forced through this gap and is caught by the shoulder 40 between the land 35 and the reduced diameter 36 of the plunger 26. Accordingly, after dispensing of the material contained within the ampule and body portion 12, the expended collapsed ampule is easily removed by withdrawing the plunger 26. The mushroom like shape of the end of the plunger and the shoulder 40 in combination with the gap formed between the diameter of the land 35 and the reduced diameter 36 caused the plunger end to grab and hold the collapsed material of the ampule 10 and body portion 12 such that it is attached to the end of the plunger 26 and therefore is withdrawn with the plunger 26. This facilitates easy removal from the barrel 28 of the expended collapsed ampule.

Figure 7:
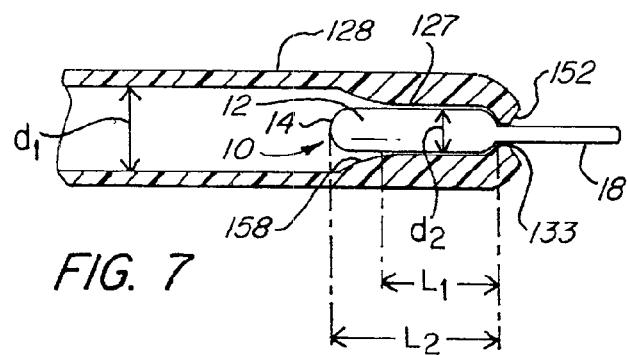
FIG. 7 is a partial section illustrating one embodiment of the present invention.

FIG. 7 is a partial cross section of another embodiment of the present invention. In this embodiment, a portion of a dispensing syringe is illustrated having a barrel 128 with different internal diameters. The barrel 128 has a larger first diameter $d_1$ and a smaller second diameter substantially equal to the diameter $d_2$ of the body portion 12 of the ampule 10. The reduced diameter portion of the barrel 128 is adjacent the opening 133 through which the nozzle 18 extends and has an axial length $L_1$ equal to a substantial portion of the axial length $L_2$ of the body 12 of the ampule 10. The transition 158 between the two diameters in the barrel 128 may be a curve or a ramp. The transition may also be a step. The rear end portion of the ampule 10 extended into the larger internal diameter portion of the barrel 128 facilitates the rear hemispherical end 14 to collapse and the initiation of rolling over the plunger end such that the dispensing of the material contained within the ampule 10 is more controlled, and the ampule body 12 collapses evenly and uniformly as the plunger advances. Additionally, the larger diameter $d_1$ greatly aids in the material of the body 12 to be forced around the outside of the plunger end as the plunger advances into the smaller diameter portion of the barrel 128. Accordingly, it is more assured that the expended collapsed ampule will attach itself to the end of the plunger so that when the plunger is withdrawn, the expended collapsed ampule is pulled out with the plunger. The larger diameter $d_1$ also facilitates collapsing of the hemispherical end portion 14 of the ampule 12 preventing initial spurting of material when being dispensed. Additionally, the barrel 128 has an angled surface or bevel 152 adjacent opening 133 to allow easier removal of the ampule 10.

Figure 8:
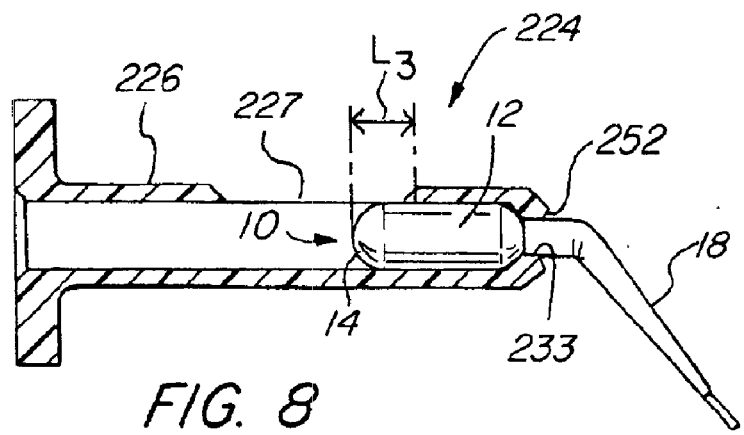
FIG. 8 is a partial cross section of another embodiment of the present invention illustrating the positional relationship of a breach.

FIG. 8 illustrates another embodiment of the present invention. The dispenser syringe 224 of this embodiment has a breach 227 within a side wall of the barrel 226. The breach 227 has an axial length sufficient to permit insertion of the ampule 10. The syringe dispenser 224 may also have bevel or angled surface 252 adjacent the opening 233 through which the nozzle 18 extends. This facilitates insertion and removal of the nozzle portion 18 of the ampule 10. The breach 227 in a side wall of the barrel 226 should be positioned close enough to the opening 233 such that a portion of the body 12 of ampule 10 extends beyond the forward end of the breach 227. This axial distance is illustrated as $L_3$. The distance $L_3$ is preferably substantially equal to a diameter of the body portion 12 of the ampule 10. The extension of the ampule 10 under or in the breach 227 facilitates collapse of the hemispherical end 14 prior to being confined by the internal diameter of the barrel 226. This has been discovered to greatly facilitate the controlled release of the material within the ampule 10 so as to prevent spurting or jerky dispensing of the material within the ampule 10 upon initial dispensing. This embodiment provides for a much more consistent and even flow during the entire dispensing sequence. This is often critical in procedures involving dentistry and placement of low viscosity materials in a patients mouth.

Figure 9:
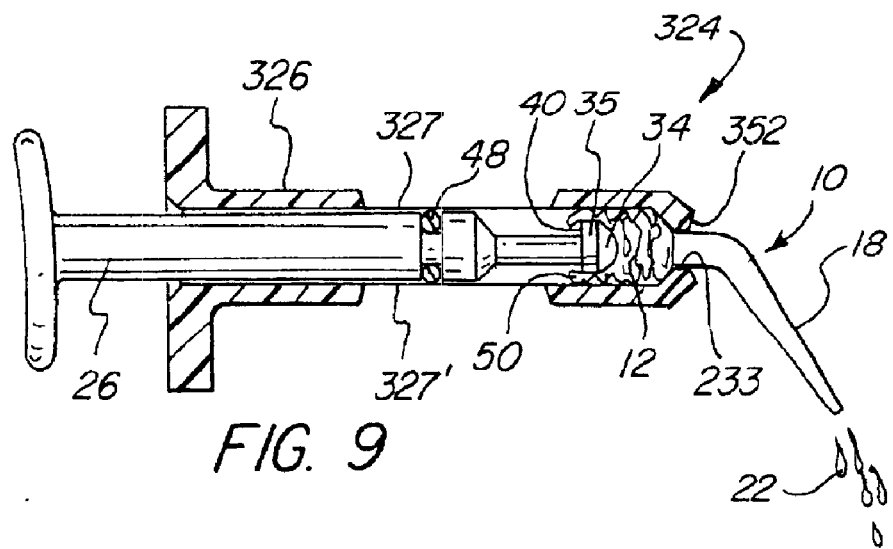
FIG. 9 is a partial cross section of another embodiment of the present invention having opposing breaches.

FIG. 9 illustrates another embodiment of a syringe dispenser 324. In this embodiment, opposing breaches 327 and 327' are formed within the barrel 236. The opposing breaches facilitate insertion and removal of the ampule 10. The ampule 10 can easily be inserted and removed with the double opposing breach configuration. The thumb and forefinger can be used to grasp the ampule on either side through the breaches and inserted into the front portion of the barrel 326 prior to advancing the plunger 26. Likewise, upon removal, the double breach permits easy grasping of the expended ampule 10. This embodiment also has a beveled or angled surface 352 adjacent opening 333 through which the nozzle 18 of the ampule 10 extends. Similar to the prior embodiments, the hemispherical plunger end 34 forces a portion of the collapsed ampule 50 between the gap in the land 50 and the internal diameter of the barrel 326 such that the expended collapsed ampule end 50 is caught or hooked onto the shoulder 40. This permits the ampule 10 to be withdrawn from the front of the barrel after being expended and when withdrawing the plunger 26. The breaches illustrated in FIG. 8 and FIG. 9 make possible the insertion and removal of an ampule without the necessity of removing the plunger 26.

Figure 10:
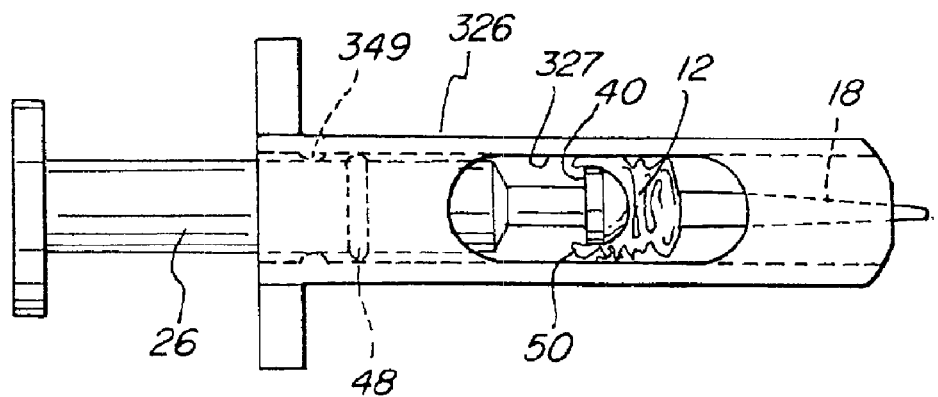
FIG. 10 is plan view illustrating an embodiment of the present invention with a e.

FIG. 10 is a top view illustrating the breach 327 and the withdrawal of the plunger 326 drawing back the body portion 12 of ampule 10. Additionally, illustrated is a detent 349 which co-acts with the O-ring 48 to prevent the plunger 26 from falling out of the end of the barrel 326 unintentionally.

Figure 11A:
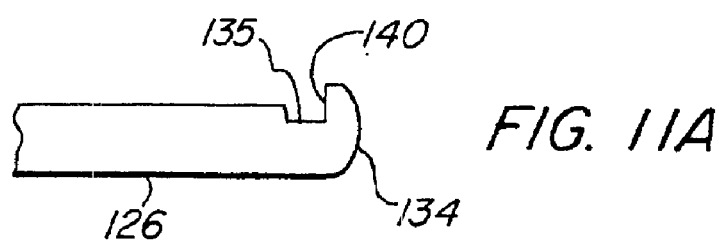
FIGS. 11A–C schematically illustrate a partial view of plunger ends of different embodiments of the present invention.
Figure 11B:
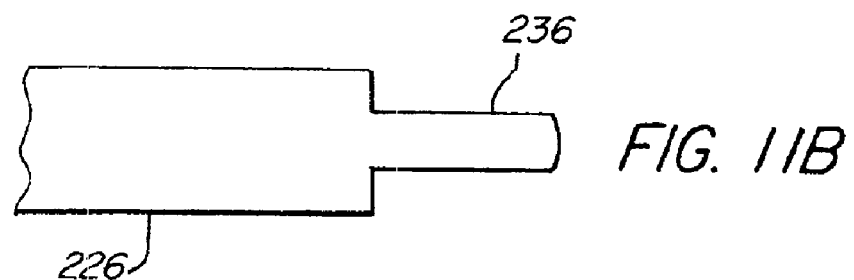
Figure 11C:
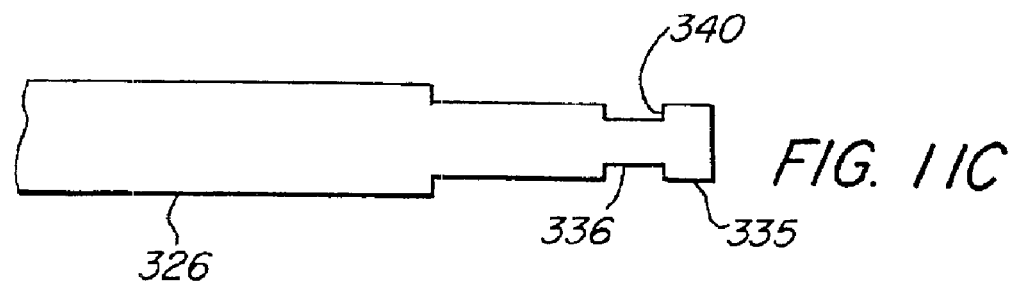

FIGS. 11A–C schematically illustrate portions of plunger ends which may be utilized in practicing the present invention. FIG. 11A illustrates the front portion of a plunger 126 having a groove 135 therein and a hemispherical front portion 134. A shoulder 140 is formed by the groove 135. The tip of the shoulder 140 may extend slightly above the surface of the plunger 126 so as when advanced the expended collapsed ampule body portion is hooked by the raised shoulder 140 facilitating removal. FIG. 11B illustrates a plunger 226 having a front portion 236 with a reduced diameter. In this embodiment, the reduced embodiment 236 has a diameter slightly smaller than a front opening in the barrel such that after extruding of the materials in the ampule with a relatively low first force on the plunger 226, the plunger 26 may be advanced with a substantially greater force so as to push the expended collapsed ampule out of the front opening of the barrel with the reduced diameter portion 236. The difference between the opening in the barrel and the reduced diameter portion 236 should be greater than twice the thickness of the plastic material from which the ampule is made. FIG. 11C illustrates another embodiment of a plunger 336. Plunger 336 has a front end having a land 335 and an adjacent groove 336 such that an inclined shoulder 340 is formed. The inclined shoulder 340 aids in grasping the expended collapsed ampule such that it can be withdrawn or removed when removing the plunger 326. While FIGS. 11A–C illustrate different embodiments of a plunger, it should be readily appreciated that other embodiments or plunger designs may easily be achieved based upon the teachings of the present invention. Other equivalent designs may be contemplated that serve the function of grasping the expended collapsed ampule so that it could be withdrawn from a barrel. In another embodiment, the plunger may be smooth.

FIGS. 12A–C illustrate another embodiment of an ampule 110. In this embodiment, a concave hemispherical sealed end 114 is formed. The concave hemispherical sealed end 114 facilitates dispensing of the material and permits a more even steady flow upon initial dispensing of the material and prevents the possibility of spurting material. Uneven flow or spurting may be more likely in the convex hemispherical sealed end embodiment illustrated in FIGS. 1–4. The use a dispensing syringe of the embodiment illustrated in FIG. 7 having a double inner diameter reduces the need for the concave hemispherical sealed end 114 of the ampule 110. FIG. 12A illustrates an ampule 110 having a body portion 112 and a nozzle 118. Nozzle 118 is sealed by seal 120. It should be appreciated that seal 120 need not take the form as illustrated, but may simply be a small spherical end to the nozzle 118, or any other equivalent seal. FIG. 12B is a plan view more clearly illustrating the ampule 110. FIG. 12C is a cross section taken along line 12C—12C in FIG. 12B and more clearly illustrates the concave hemispherical sealed end 114 of this embodiment of the present invention. Material 122 is contained within the ampule 110.

FIGS. 13A–C illustrate yet another embodiment of the present invention. Ampule 210 comprises a bellows body portion 212 having a front collar 213 at one end and a sealed end 214 at the other. The sealed end 214 also has a recess 214' therein. The recess 214' is coaxial with the body portion 212 and is sized to mate with the end of a plunger, preventing the sealed end 214 from deviating axially during compression of the bellows body portion 212 during dispensing the material 222 contained therein out of nozzle 218.

Figure 14A:
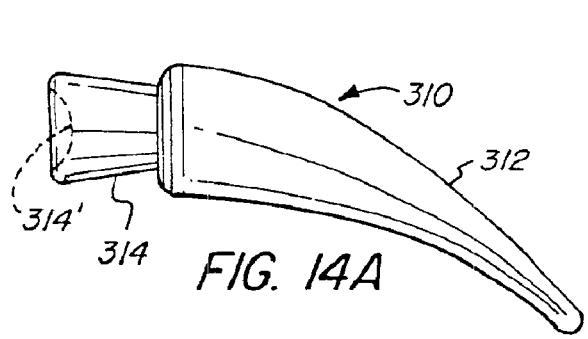
FIG. 14A is a side elevational view of another embodiment of an ampule of the present invention.
Figure 14B:
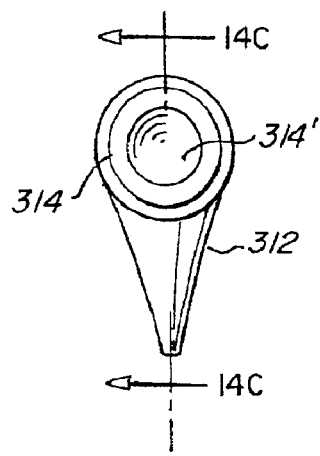
FIG. 14B is a rear elevational view of the ampule illustrated in FIG. 14A.
Figure 14C:
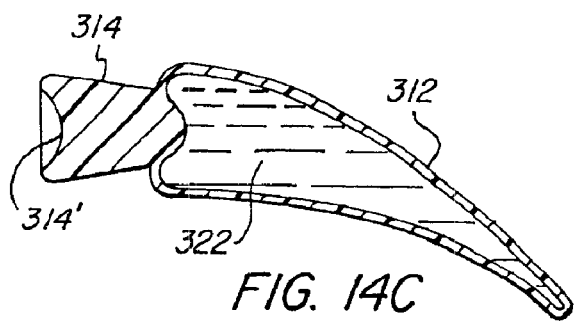
FIG. 14C is a cross section taken along lines 14C—14C in FIG. 14B.

FIGS. 14A–C illustrate another embodiment of the present invention. Ampule 310 comprises a curved body portion 312 having a sealed end with an attached piston 314. Piston 314 has a concave portion 314'. The body portion 312 may initially be sealed at the dispensing end and easily cut, pierced, broken off, or snapped off to dispense the material 322 contained therein. The attached piston 314 has an inclined surface or is conically shaped such that upon advancing, the walls of the body portion 312 are rolled along the surface of the plug or piston 314. This assures that the walls of the body portion 312 are uniformly and evenly folded over upon themselves, preventing spurting or jerky dispensing of the material 322 contained therein. Preferably, the axial length of the piston 314 is approximately equal to the greatest lateral dimension of the body portion 312.

Figure 15:
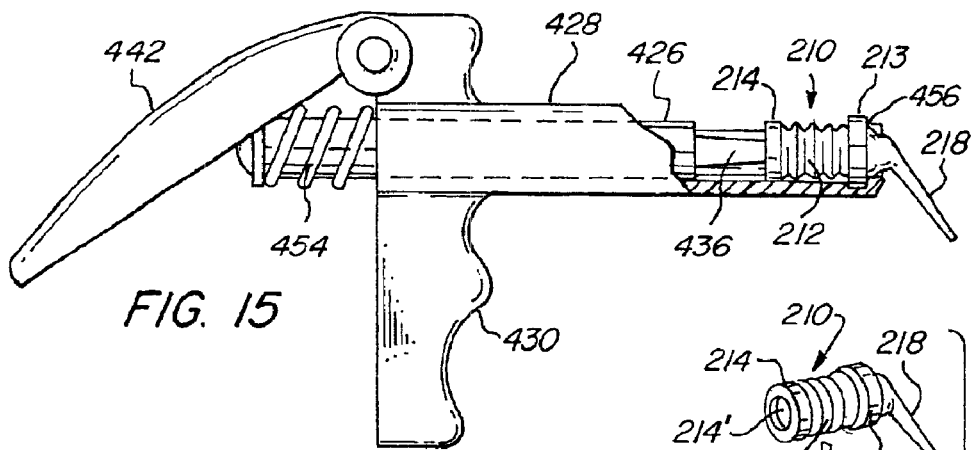
FIG. 15 is a side elevational view in partial section of a syringe having a mechanical advantage.

FIG. 15 illustrates an embodiment of the present invention utilizing a syringe having a mechanical advantage. A barrel 428 has a handle 430 thereon. Lever 442 is pivotally connected to the handle 430 and has a cam surface that advances the plunger 426. The plunger 426 may have a spring 454 on either end thereof so as to bias the plunger away from the dispensing end. The plunger 426 also has a reduced diameter section 436 sized to mate with the rear of an ampule 210. The ampule 210 is placed through a breach adjacent the end of the barrel 428. A shoulder 456 on the end of the barrel 428 holds the collar 213 of the ampule 210. The rear end 214 of the ampule 210 is advanced by the reduced diameter portion 436 of the plunger 426. The bellows body portion 212 collapses axially. The collar 213 in combination with the sealed rear end 214 permit the breach to be placed adjacent the front of the barrel so as to greatly facilitate insertion and removal of the ampule 210 in this embodiment. The bellows body 312 permits the use of a more rigid plastic material which facilitates the dispensing of materials that may have slightly more viscosity than a liquid or a gel. The recess 214' mating with the reduced diameter end 436 of the plunger 426 helps to maintain axial alignment of the bellows body portion 212 of the ampule 210.

Figure 16:
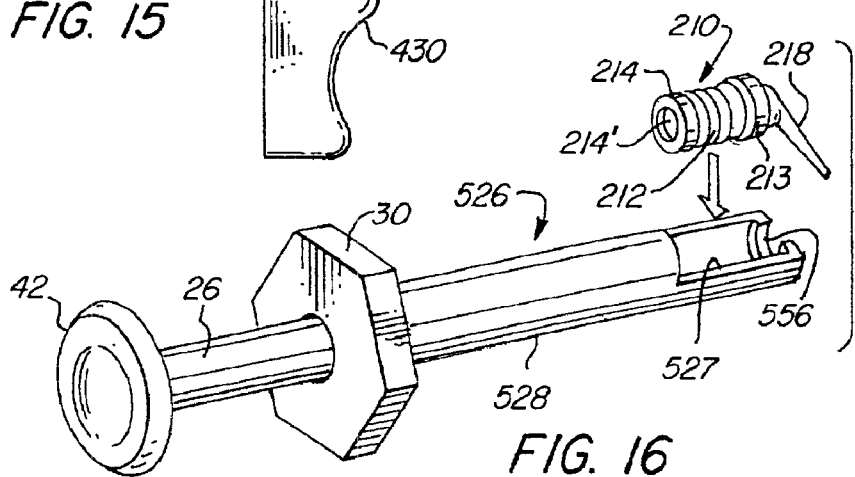
FIG. 16 is a perspective view illustrating another embodiment of the present invention.

FIG. 16 is a perspective view illustrating another embodiment of the present invention having a barrel 528 with a breach 527 therein and a shoulder 556 adapted to mate with a collar 213 on ampule 212. The syringe dispenser 526 does not have a mechanical advantage. A plunger 26 having a pad 42 thereon is advanced forward striking the sealed rear end 214 compressing the bellows body portion 212 of the ampule 210 dispensing a material from nozzle 218.

Accordingly, it should be appreciated from the above description that the present invention has several embodiments that greatly facilitate the dispensing of low viscosity materials including liquids and gels in a controlled manner. The present invention has the benefit of utilizing ampules that may be relatively inexpensively manufactured providing a unit dose or a predetermined dose of material that can be easily applied in a controlled, even manner without spurting or jerkiness in motion. This permits very fine control in the dispensing of a liquid or a gel without the need of a separate applicator, such as a brush or swab.

While several embodiments of the present invention have been illustrated and described, it will be obvious to those skilled in the art to apply the teachings of the present invention to their respective arts. Additionally, although the preferred embodiments have been illustrated and described, it will be obvious to those skilled in the art that various modifications may be made without departing from the spirit and scope of this invention.

What is claimed is:

1. A syringe system for dispensing a material comprising:
   a collapsible ampule containing the material to be dispensed, said collapsible ampule having a body portion with a first longitudinal length and a nozzle portion with a second longitudinal length;
   a barrel having an inner diameter adapted to receive said collapsible ampule, said barrel having a first breach and a second breach opposing the first breach spaced a first distance from one end of said barrel, said first distance being less than the second longitudinal length of the nozzle portion of said collapsible ampule, whereby the nozzle portion of said collapsible ampule is capable of being used to move said collapsible ampule under the first and second breach in said barrel facilitating removal of said collapsible ampule after the material is dispensed; and
   a plunger sliding within said barrel,
   whereby the collapsible ampule is inserted and removed from either the first or second breach.

2. A syringe system for dispensing a material as in claim 1 wherein:
   said collapsible ampule comprises a collapsible body, a concave rear end attached to said collapsible body, and a temporarily sealed dispensing nozzle attached to said collapsible body.

3. A syringe system for dispensing a material as in claim 2 wherein:
   said temporarily sealed dispensing nozzle comprises a snap off seal.

4. A syringe system for dispensing a material as in claim 1 further comprising:
   a snap off seal on said nozzle portion.

5. A syringe system for dispensing a material comprising:
   a collapsible ampule containing the material to be dispensed, said collapsible ampule having a body portion with a first longitudinal length and a nozzle portion with a second longitudinal length;
   a barrel having an inner diameter adapted to receive said collapsible ampule, said barrel having a breach spaced a first distance from one end of said barrel, said first distance being less than the second longitudinal length of the nozzle portion of said collapsible ampule and greater than a majority of the first longitudinal length of the body portion, whereby the nozzle portion of said collapsible ampule is capable of being used to move said collapsible ampule under the breach in said barrel facilitating removal of said collapsible ampule after the material is dispensed and facilitates controlled release of the material; and a plunger sliding within said barrel, whereby the collapsible ampule is inserted and removed from the breach and the nozzle portion is directed through an opening in a closed end of the barrel.

6. A syringe system for dispensing a material as in claim 5 further comprising:

a detent, said detent preventing said plunger from falling out of said barrel.

7. A syringe system for dispensing a material as in claim 5 further comprising:

a bevel placed on a dispensing end of said barrel, whereby insertion and removal of the nozzle portion of said collapsible ampule is facilitated.

8. A syringe system for dispensing a material as in claim 5 wherein:

a rear portion of said collapsible ampule extends a second longitudinal distance greater than an outer diameter of the body portion of said collapsible ampule under the breach.

9. A syringe system for dispensing a material as in claim 5 wherein:

said collapsible ampule comprises a collapsible body, a concave rear end attached to said collapsible body, and a temporarily sealed dispensing nozzle attached to said collapsible body.

10. A syringe system for dispensing a material as in claim 9 wherein:

said temporarily sealed dispensing nozzle comprises a snap off seal.

11. A syringe system for dispensing a material as in claim 5 further comprising:

a snap off seal on said nozzle portion.

* * * * *